US006797498B1

(12) United States Patent
Bachmann et al.

(10) Patent No.: US 6,797,498 B1
(45) Date of Patent: Sep. 28, 2004

(54) B, B-CAROTENE 15, 15'-DIOXYGENASES, NUCLEIC ACID SEQUENCES CODING THEREFOR AND THEIR USE

(75) Inventors: Heinrich Bachmann, Wintersingen (CH); Roland Brugger, Lörrach (DE); Arno Martin Friedlein, Bad Krozingen (DE); Gabriele Margarethe Wirtz, Wuppertal (DE); Wolf-Dietrich Woggon, Binningen (CH); Adrian Wyss, Möhlin (CH); Markus Wyss, Liestal (CH)

(73) Assignee: DSM Nutritional Products, Inc., Parsippany, NJ (US)

( * ) Notice: Subject to any disclaimer, the term of this patent is extended or adjusted under 35 U.S.C. 154(b) by 0 days.

(21) Appl. No.: 09/504,393

(22) Filed: Feb. 15, 2000

(30) Foreign Application Priority Data

Feb. 22, 1999 (EP) .............................. 99103382

(51) Int. Cl.[7] .......................... C12N 9/02; C12N 15/00; C12N 1/20; C07H 19/00; C07H 21/04
(52) U.S. Cl. ................ 435/189; 435/252.3; 435/320.1; 435/325; 435/410; 435/6; 435/183; 536/23.1; 536/23.2; 536/22.1
(58) Field of Search ........................ 435/6, 190, 252.3, 435/183, 71.1, 252.9, 440, 320.1, 189, 325, 410; 536/23.2, 24.1–24.33, 24.5, 23.1, 22.1

(56) References Cited

FOREIGN PATENT DOCUMENTS

WO    WO 93/23538    11/1993

OTHER PUBLICATIONS

Thorhjornsen et al. GenEmbl database—Accession #AF073473 (1998).*
Leuenberger et al. The reaction mechanism of the enzyme catalyzed central cleavage of B–carotene to retinal. Angew. Chem INt. Ed, vol. 40, No. 14, pp. 2614–2617 (2001).*
Functional and evolutionary relationships among diverse oxygenases. Annu. Rev. Microbiol. vol. 46, pp. 565–601 (1992).*
Pfam web printout. Dioxygenase and Monooxygenase.*
Sharma, R.V. et al., "Studies On The Metabolism Of β–Carotene and Apo–β–Carotenoids In Rats and Chickens," *Biochmica et Biophysica Acta*, vol. 486, pp. 183–194 (1977).
Laksmanan, et al., "Purification and properties of carotene 15, 15'–dioxygenase of rabbit intestine," *Journal of Lipid Research*, vol. 13, pp. 477–482 (1972).
Devery, et al., "β–Carotene–15,15'–dioxygenase (EC 1.13.11.21) isolation reaction mechanism and an improved assay procedure," *British Journal of Nutrition*, vol. 72, pp. 397–414 (1994).
Wolf, "The Enzymatic Cleavage of β–Carotene: Still Controversial," *Nutrition Reviews*, vol. 53, No. 5, pp. 134–137 (1995).

* cited by examiner

Primary Examiner—Ponnathapu Achutamurthy
Assistant Examiner—Yong D. Pak
(74) Attorney, Agent, or Firm—Bryan Cave LLP

(57) ABSTRACT

Nucleic acid sequences coding for a protein having β,β-carotene 15,15' enzyme activity and their uses in diagnostics, the synthesis of vitamin A and methods for the introduction of the β,β-carotene 15,15' enzyme cDNA into host cells are disclosed.

24 Claims, 12 Drawing Sheets

Figure 3
No. 2

Seq. ID

```
  1 CGGATCCACT AGTAACGGCC GCCAGTGTGG TGGAATCCAT CCTTCTATGT
 51 AACAGGAAAG AGCTGTTCTT AGCCCAGAGA GGAGGGCACC GTACGCCTGC
101 AGGAGCAGCT GGGTAGAGGA CACAGGAGAG CGATGGAGAC AATATTTAAC
151 AGAAACAAAG AAGAGCATCC AGAGCCCATA AAAGCTGAGG TGCAAGGTCA
201 GTTGCCCACT TGGTTGCAAG GGGTACTTCT CCGAAATGGC CCAGGGATGC
251 ACACAATAGG GGACACTAAA TACAACCACT GGTTTGATGG CTTGGCTCTG
301 CTGCACAGCT TCACGTTTAA AAATGGTGAA GTTTACTACA GAAGTAAGTA
351 CCTCCGAAGT GACACATACA ACTGCAATAT AGAAGCAAAC CGAATCGTGG
401 TGTCTGAGTT TGGAACCATG GCTTATCCGG ATCCATGCAA AAACATATTT
451 GCCAAGGCAT TCTCATACTT ATCTCACACC ATTCCTGAGT TCACGGACAA
501 CTGCCTGATC AACATTATGA AAACTGGGGA TGATTATTAT GCTACCAGTG
551 AGACTAACTT CATCAGAAAA ATTGATCCAC AGACTCTGGA GACACTAGAT
601 AAGGTAGACT ACAGCAAATA TGTAGCTGTA AACTTGGCAA CTTCTCACCC
651 ACACTATGAC AGTGCTGGAA ATATTCTCAA CATGGGTACT TCAATTGTTG
701 ATAAAGGGAG AACAAAATAT GTTCTCTTTA AGATCCCTTC CTCTGTACCA
751 GAAAAGAAA AGAAGAAATC TTGTTTTAAA CACCTGGAAG TAGTATGCTC
801 CATCCCTTCT CGCTCCCTGC TCCAACCAAG CTACTACCAC AGCTTTGGAA
851 TCACAGAAAA TTATATTGTG TTCATAGAGC AGCCATTTAA ACTGGATATT
```

```
 901  GTCAAACTGG CAACTGCCTA CATCCGAGGT GTGAACTGGG
CTTCCTGCCT

951  TTCCTTTCAT AAGGAGGATA AGACGTGGTT TCACTTTGTA
GACAGAAAGA

1001  CGAAAAAGA AGTATCCACC AAGTTTTACA CTGATGCTTT
GGTGCTTTAT

1051  CACCACATAA ATGCTTACGA AGAAGATGGC CACGTTGTTT
TTGATATCGT

1101  TGCCTACAGA GACAATAGCT TGTACGATAT GTTTTACTTA
AAAAAACTGG

1151  ACAAAGACTT TGAAGTGAAC AACAAGCTTA CCTCCATCCC
AACCTGCAAG

1201  CGCTTTGTTG TGCCTCTGCA GTATGACAAG GATGCAGAAG
TAGGTTCTAA

1251  TTTAGTCAAA CTTCCAACTT CCGCAACTGC TGTAAAAGAA
AAAGATGGCA
1301  GCATCTATTG TCAACCTGAA ATATTATGTG AAGGGATAGA
ACTGCCTCGT

1351  GTCAACTATG ACTACAATGG CAAAAAATAC AAGTATGTCT
ATGCAACAGA

1401  AGTCCAGTGG AGCCCAGTTC CTACAAAGAT TGCAAAACTG
AATGTCCAAA

1451  CAAAGGAAGT ACTGCACTGG GGAGAAGACC ACTGCTGGCC
CTCAGAGCCC

1501  ATCTTTGTTC CCAGCCCCGA TGCAAGAGAA GAGGATGAAG
GTGTTGTTTT

1551  GACCTGTGTT GTGGTGTCTG AGCCAAATAA AGCACCCTTC
CTACTCATCT

1601  TGGATGCTAA AACATTCAAA GAATTGGGCC GAGCCACAGT
TAACGTAGAA

1651  ATGCATCTGG ACCTGCATGG GATGTTTATA CCACAGAATG
ATTTGGGGGC

1701  TGAGACGGAA TAAAACGCTA TTGATCCGAC TACACAAACT
GAGACAACTT

1751  TCTACTGAAC ATGAGTTAAT ATCCCTTTTA CCATTCAAGA
ACAACCATAT

1801  AACGACACAA AATGACTATG TATAATCTCT TAAATAATAG
ATATAATCCT

1851  TTTAAGGCAC AGCGATGAGT TTTACTACAG GTAACGATAT
GCACAACTGG
```

1901  CATATAACTA TTCCAAAAGA AGAAGAACGA TCAGTGTTTT
AGAAGTGCTA

1951  ATGTTGTACA TAACGGCGGC AGAGGGAACA GGAGAGAAAG
GTAACGGGAA

2001  TATTTAATAG AATATAGATT TCTGAGCAAA TGAAGTGCAG
TATTTATGGT

2051  GTGATGCATG GCATGAGTCA CATAGGTCTG CAGCTCATGT
ATCTTTTAGA

2101  GATCGTTTCA AGATTGCAGC TTGTGATGCA AGTTTTCTCC
AGCCAGAAAA

2151  CCTCATTTTA AACCATCTGC TACTGGTAAT TCATACCAAT
GCATTTTCTT

2201  GGTGCTCGAT TTACACTATA ACCAAGTTA AGTATTACAT
TCAGGTGCTA

2251  CAACTTTCTA ATTTACAACC GAAACAAACA AGCAAACAGC
ACTTGCTTTG

2301  CTAATAACCC CATGGTGTAT TTTTCCTTTT TATGATGACA
AAACCAAGTA

2351  CATATGGTTT TATGTAGCAT TCAATTATAC TTCAGTGCTA
TTCCATCCTA

2401  ATGTTATAAG CAATTTGTAT TTAAATCAGT TTTCCTTGAG
AATATCTGAC

2451  ATAACATTTT GTGTAATGAG ATGACTATGT TGTCTAAAGA
TGAACAGGAA

2501  TGTATCTTTT ATTAGTATTG TTAATTGTGT TACTAATACT
ATGCATATGA

2551  ATGAGAGCAA TGTATTTCTA GGAGAACTCA GATATACATT
CAACAATTTC

2601  TGTAGGTGAA AATGCATTTA CTGATGAAAG TTGAATCGTT
AATGAGGGAG

2651  AAAACTGGGT ATCCATCCAT CCAACTATGT TAGGTGTTCA
CCTGGTCTGT

2701  ATGTGACACC ACGCTGTTTG GGTATCTCTC ACTTTCACAT
ACCTGTTCTC

2751  ATGGTTTCTG CTACTCACTG TATTTGCAG GAGAGAAACA
AAATGAAATC

2801  ACTGTCACTT ACTATCGCCC CATCACATAA GAACAATGGG
GCTTTGGTGA

```
    2851  CTTGTTCATG ATTACATAAG ATGTTTGCAG CAGAGCAGCA
ATAGAACCAA

2901  CACCATCCAC AGTTCTTGCT TGCTCTGTTA TGACTCCCTT
TGCTGTCTTT

2951  ATGGTTTGCA TGTATGAAGA ATACACTGCC TAATTCTAAT
GTTAAAAAGT

3001  CACTGGGGTC AGATCTAGAG CTTAAGTAAG CAGTCTGGGG
TTTTCAAATG

3051  TTTATATGTT CCATAAAATG GAAATAAACA CCTCCATAAT
AAAAAAAAAA

3101  AAAAAAAAA A
```

Figure 4  Seq. ID
No. 1

```
  1 METIFNRNKE EHPEPIKAEV QGQLPTWLQG VLLRNGPGMH
TIGDTKYNHW

51 FDGLALLHSF TFKNGEVYYR SKYLRSDTYN CNIEANRIVV
SEFGTMAYPD

101 PCKNIFAKAF SYLSHTIPEF TDNCLINIMK TGDDYYATSE
TNFIRKIDPQ

151 TLETLDKVDY SKYVAVNLAT SHPHYDSAGN ILNMGTSIVD
KGRTKYVLFK

201 IPSSVPEKEK KKSCFKHLEV VCSIPSRSLL QPSYYHSFGI
TENYIVFIEQ

251 PFKLDIVKLA TAYIRGVNWA SCLSFHKEDK TWFHFVDRKT
KKEVSTKFYT

301 DALVLYHHIN AYEEDGHVVF DIVAYRDNSL YDMFYLKKLD
KDFEVNNKLT

351 SIPTCKRFVV PLQYDKDAEV GSNLVKLPTS ATAVKEKDGS
IYCQPEILCE

401 GIELPRVNYD YNGKKYKYVY ATEVQWSPVP TKIAKLNVQT
KEVLHWGEDH

451 CWPSEPIFVP SPDAREEDEG VVLTCVVVSE PNKAPFLLIL
DAKTFKELGR

501 ATVNVEMHLD LHGMFIPQND LGAETE
```

Figure 5    Seq ID No. 4 and Seq ID No. 5

```
 57  10 EEHPEPIKAEVQGQLPTWLQGVLLR..NGPGMHTIGDTKYNHWFDGLALL
        ||   |:| | |.:| || |  |||   |||:  :|   :  | ||| |||
 69  20 EELSSPLTAHVTGRIPLWLTGSLLRCFTGPGLFEVGSEPFYHLFDGQALL 105  58 HSFTFKNGEVYYRSKYLRSDTYNCNIEANRIVVSEFG...TMAYPDPCKNI
        | | || | | |    :::|.| |    .   |||:.|||  | |:|||||||
119  70 HKFDFKEGHVTYHRRFIRTDAYVRAMTEKRIVITEFGFTTCAFPDPCKNI 155 106 FAKAFSYLSHTIPEFTDNCLINIMKTGDDYYATSETNFIRKIDPQTLETL
        |.: |||    | ||| |:|:    |:||||  |||||  ||.|:||||:
167 120 FSRFFSYFRGV..EVTDNALVNVYPVGEDYYACTETNFITKINPETLETI 203 156 ..DKVDYSKYVAVNLATSHPHYDSAGNILNMGTSIVDKGRTKYVLFKIPS
        .||  ||.|| ||.||| :.  |   :  | |         |  :  |||
217 168 FTKQVDLCNYVSVNGATAHPHIENDGTVYNIGNCFGKNFSIAYNIVKIPP 253 204 SVPEKEKKKSCFKHLEVVCSIPSRSLLQPSYYHSFGITENYIVFIEQPFK.
        :||  ||  |  |:|     |   .||| ||||:| |||||:|  |  |
266 218 LQADKEDPISKFTS.EIVVQFPCSDRFKPSYVHSFGLTPNYIVFVETPVK 300 254 LDIVKLATAY.IRGVNWASCL.SFHKEDK.TWFHFVDRKTKKEVSTKFYT
        :.: |  ..: : ||: |  || |   | |  |:|  || ..  |: |
316 267 INLFKFLSSWSLWGANYMDCFESFTNETMGVWLHIADKKRKKYLNNKYRT 344 301 DALVLYHHINAYEEDGHVVFDIVAYRDNSL...YDMFYLKKLDKDFE...
        |:|||| ||:.|  .: |:  ::       |   ||  |  ...|
366 317 SPFNLFHHINTYEDNGFLIVDLCCWKGFEFVYNYFTLYLANLRENWEEVK 391 345 VNNKLTSIPTCKRFVVPLQYDKDAEVGSNLVKLP.TSATAV..KEKDGSI
        | :    |    :|:.||  || |: | ||| || |.|||:   :. .|
415 367 KNARKAPQPEVRRYVLPLNIDK.ADTGKNLVTLPNTTATAILCSDEFTTI 436 392 YCQPEILCEG....IELPRVNYD.YNGKKYKYVYATEVQWSPVPTKIAKL
        : :|||:| |     | |.:|| | ||| |   . || ::  ||
464 416 WLEPEVLFSGPRQAFEFPQINYQKYCGKPYTYAYGLGLNHF.VPDRLCKL
```

```
437 NVQTKEVLH..WGEDHCWPSEPIFVPSPDAREEDEGVVLTCVVVSEPNKA 484
    ||.|||     ||    :|||||||  |||  |||:||||. ||
465 NVKTKETWFTVWQEPDSYPSEPIFVSHPDALEEDDGVVLSVVVSPGAGQK 514

485 P.FLLILDAKTFKELGRA...TVNVEMHLDLHGMF 515
    | :||||.||    |.  ||  ||  : . .  ||:|
515 PAYLLILNAKDLSEVARAEFTVEINIPVTFHGLF 548
```

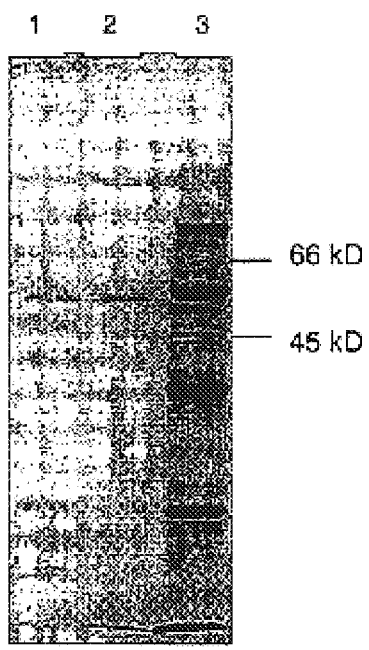
Fig. 6 shows a 10% polyacrylamide gel with E.coli expressed β,β-carotene 15,15'-dioxygenase after affinity tag purification; lane 1 and lane 2: 2 fractions from the $Co^{2+}$-chelate column showing the main band at 60 kD; lane 3: low range molecular weight marker (Bio Rad).

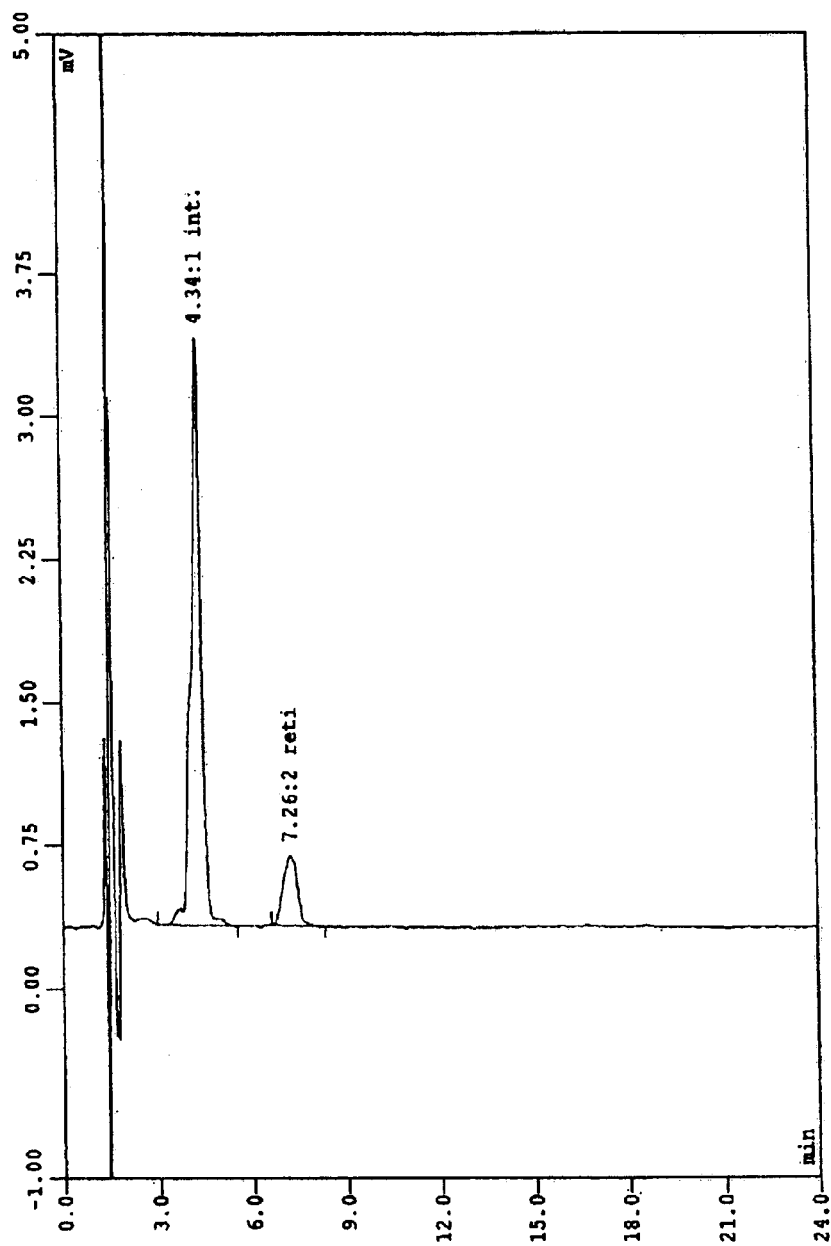
Fig. 7 shows an HPLC profile of the reaction mixture at the end of an actvity assay for the β,β-carotene 15,15'-dioxygenase following the procedure in example 1. The first peak in the chromatogram represents the internal standard, while the second peak corresponds to retinal as the only product formed during the central cleavage with β-carotene as substrate.

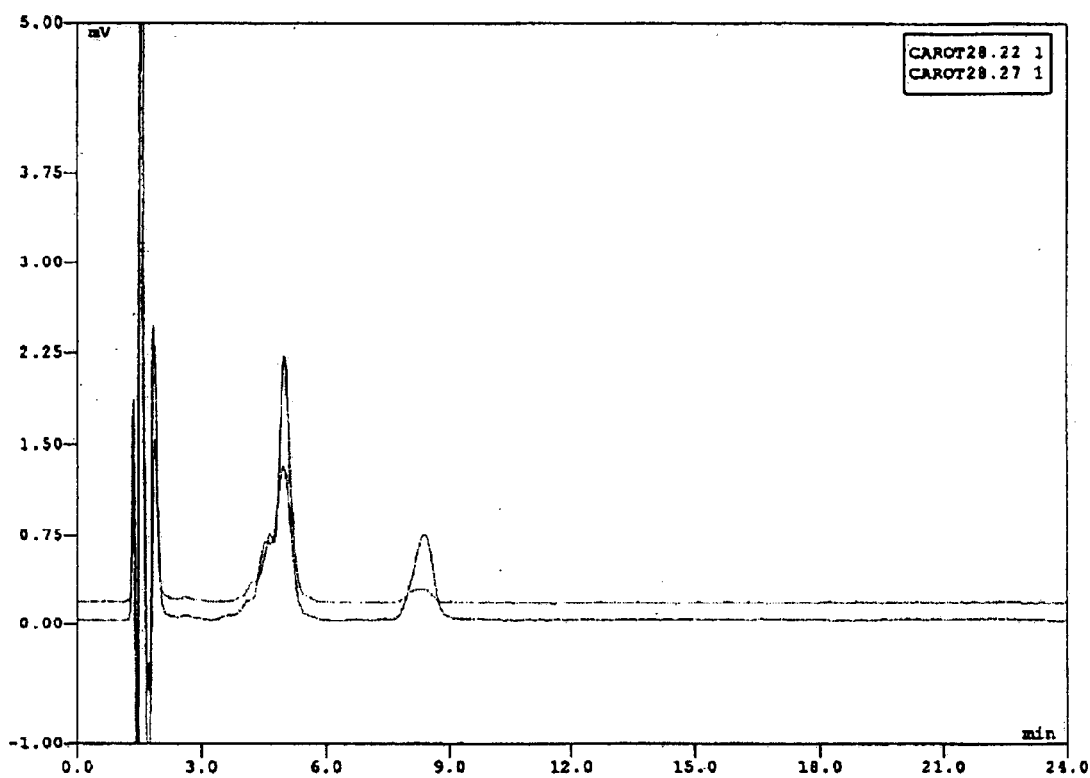
Fig. 8 confirms that the product peak in Fig. 7 is indeed retinal. A sample which was positive in the activity assay (green chromatogram) was spiked with retinal and analysed in second HPLC run (red chromatogram). The chromatograms of the two runs were then overlayed.

B, B-CAROTENE 15, 15'-DIOXYGENASES, NUCLEIC ACID SEQUENCES CODING THEREFOR AND THEIR USE

FIELD OF THE INVENTION

The present invention concerns the cloning of β,β-carotene 15,15' enzyme (EC 1.13.11.21), the enzyme responsible for the cleavage of β-carotene leading to vitamin A. The term vitamin A as defined in the present invention comprises a class of compounds including retinal, retinol, 3-dehydroretinol, retinoic acid, the isomers from these compounds as well as retinylesters. Proteins having β,β-carotene 15,15' enzyme activity and nucleic acid sequences coding therefore can be used in different fields including but not limited to diagnostics, the technical production of vitamin A, the generation of transgenic plants in order to produce vitamin A in fruits and vegetables, or gene therapy.

SUMMARY OF THE INVENTION

In one embodiment of the present invention, a polypeptide having β,β-carotene 15,15' enzyme activity is provided. This polypeptide includes SEQ ID NO: 1 or a polypeptide having β,β-carotene 15,15' enzyme activity and being at least 60% homologous to SEQ ID NO: 1 as determined by the Wisconsin Sequence Analysis Package GCG, Version 9.1 (1997).

The present invention also includes a nucleic acid sequence encoding the polypeptide defined above, such as for example, SEQ ID NO: 2 or a fragment thereof Another embodiment of the invention is a primer for amplifying a gene coding for a protein having β,β-carotene 15,15' enzyme activity which includes a nucleic acid sequence as defined above.

A probe is also provided for detecting a gene coding for a protein having β,β-carotene 15,15' enzyme activity. This probe includes a nucleic acid sequence as defined above.

A test kit is also provided for amplifying and/or detecting a gene or a fragment thereof coding for β,β-carotene 15,15' enzyme. The test kit includes at least one primer as defined above. The test kit may also include at least one probe as defined above alone, or in combination with at least one primer according to the present invention.

Another embodiment of the invention is an antibody which specifically reacts with a polypeptide as defined above.

An immunoassay is also provided for the detection and/or quantification of β,β-carotene 15,15' enzyme. This immunoassay includes at least one antibody as set forth above.

A process is also provided for the production of vitamin A. This process includes enzymatically cleaving β-carotene by a polypeptide as described above.

Another embodiment is a method for introducing a β,β-carotene 15,15' enzyme cDNA into a host cell. This method includes inserting a cDNA coding for a polypeptide as described above into a vector suitable for the host cell and introducing the vector into the host cell.

A host cell is also provided. This host cell may be obtained by the method set forth above. The host cell includes a β,β-carotene 15,15' enzyme cDNA obtained from another species.

Another embodiment of the invention is a polynucleotide which encodes β,β-carotene 15,15' enzyme and includes the sequence of SEQ ID NO: 2.

A vector is also provided which includes the sequence of SEQ ID NO: 2. A host cell is also provided which has been transformed with this vector.

The present invention also includes a polypeptide having β,β-carotene 15,15' enzyme activity, which polypeptide contains the amino acid sequences of SEQ ID Nos: 1 or4.

A primer set is also provided for amplifying a polynucleotide encoding β,β-carotene 15,15' enzyme. This primer set includes SEQ ID NO: 8 as a 5' primer and a SEQ ID NO: 9 as a 3' primer. Another primer set for amplifying a polynucleotide encoding β,β-carotene 15,15' enzyme is also provided which includes a polyT/Not reverse primer and SEQ ID NO: 10 as a forward primer.

The present invention also includes a kit for amplifying and/or detecting a polypeptide or fragment thereof encoding β,β-carotene 15,15' enzyme. This kit includes at least one primer selected from SEQ ID Nos: 8, 9, and 10.

BRIEF DESCRIPTION OF THE DRAWINGS

FIG. 3 shows the cDNA sequence (SEQ ID NO: 2) for β,β-carotene 15,15 enzyme which has a length of 3090 base pairs excluding the poly A tail. 132 base pairs are 5' nontranslating sequence, the coding sequence has 1578 base pairs and the 3' nontranslating sequence 1380 base pairs, respectively. A putative poly A signal is found at position 3073.

FIG. 4 shows the derived amino acid sequence (sequence ID No. 1) of β,β-carotene 15,15' enzyme derived from chicken having 526 residues. The amino acid sequence is given in the one letter code.

FIG. 5 shows a comparison of the β,β-carotene 15,15' enzyme amino acid sequence (SEQ ID NO: 4) with a protein having the designation RPE65 (SEQ ID NO: 5) which was found by a sequence comparison in EMBL Genbank as the protein having the highest homology to the β,β-carotene 15,15' enzyme of the present invention.

FIG. 6 shows two fractions of β,β-carotene 15,15' enzyme eluted from a $Co^{2+}$-chelate column. In lanes 1 and 2 two different fractions were loaded and lane 3 is a low range molecular weight marker.

FIG. 7 shows an HPLC analysis of an activity test of β,β-carotene 15,15' enzyme which was cloned and expressed in E. coli.

FIG. 8 is a chromatogram demonstrating that the peak from FIG. 7 representing the only product of the enzymatic cleaving is retinal.

DETAILED DESCRIPTION OF THE INVENTION

Figure 1:
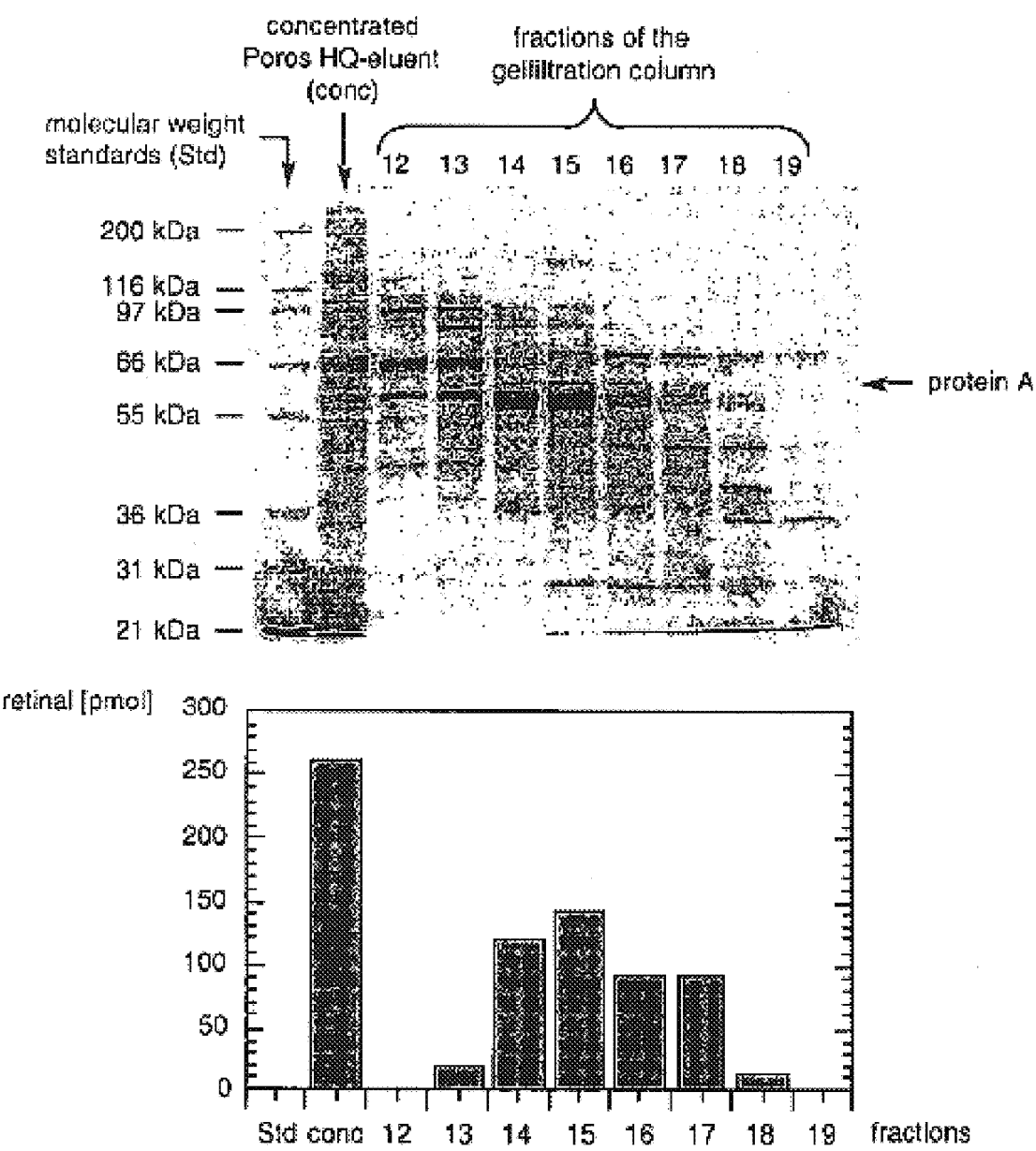
FIG. 1 shows the result from the last step of purification of β,β-carotene 15,15' enzyme from the small intestine of chicken. The SDS-PAGE pattern and β,β-carotene 15,15' enzyme activity of individual fractions from the gel permeation chromatography run are shown. On the gel, the protein A marked by an arrow correlated best with the β,β-carotene 15,15' enzyme activity. It was therefore chosen for further amino acid sequence analysis. The abbreviations have the following meaning: Std.: molecular weight standard; conc.: concentrate loaded onto the gel permeation chromatography column.

Vitamin A is essential for man and animal and is largely formed in most organisms from its precursor carotenoids which, by themselves, can only be formed in plants, in photosynthetic active microorganisms and some other microorganisms. Man and most animals (in particular herbivores and omnivores) are able to convert such carotenoids, also called provitamins A, enzymatically into vitamin A. The most important enzyme for this process is the β,β-carotene 15,15' enzyme (EC 1.13.11.21). The enzyme is located in the cytosol and forms retinal from β-carotene, as the principal substrate, in presence of oxygen according to scheme 1.

Scheme 1:

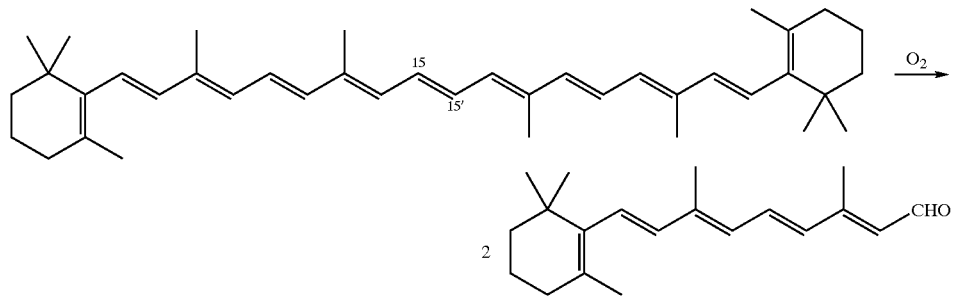

The enzyme β,β-carotene 15,15' enzyme is characterized by generating 2 mols retinal from 1 mol of β-carotene by central cleavage. But the enzyme is also able to convert a wide range of carotenoids into vitamin A-active compounds, as shown in scheme II:

Scheme II:

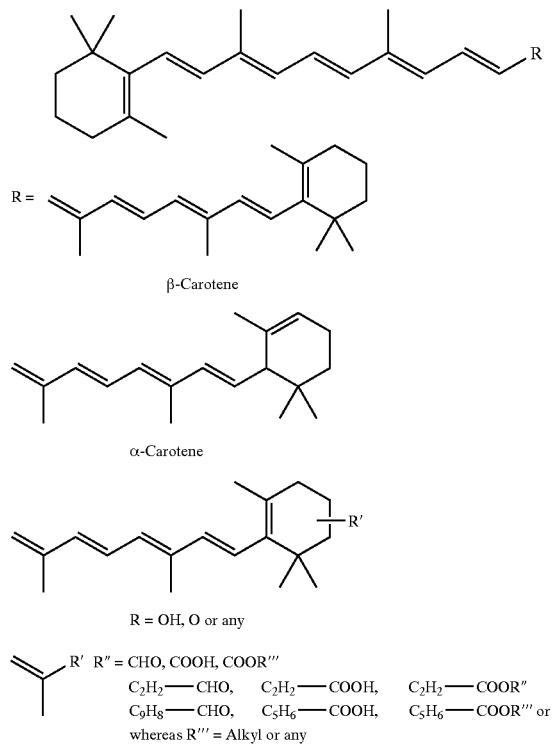

Highest known enzymatic activity is found in the intestine of herbivores, especially in duodenum. In other tissues like liver, lung, kidney and brain β,β-carotene 15,15' enzyme is also detectable. Starting in 1955, many attempts have been undertaken to purify and characterize the enzyme by biochemical methods (Goodman (1965 and 1966), Fidge (1969), Laksmanan (1972), Sharma (1977) and Devery & Milborrow (British Journal of Nutrition (1994) 72, p. 397–414). However, none of these attempts has been successful. Specific activities of 600 pmol retinal formed/mg protein per hour have not been surpassed.

In the course of the present invention it was possible to purify the chicken enzyme to such a degree that a partial amino acid sequence could be obtained. The enzyme was enriched 226-fold, yielding a specific activity of 2500 pmol/h/mg. On a polyacrylamide gel of fractions from the final gel filtration run 15 bands were visible after Coomassie blue staining. Two bands correlated with the enzymatic activity profile of the β,β-carotene 15, 15' enzyme. With the first protein Edman sequencing and with the second MS spectroscopy was performed. Tryptic ingel digestion and subsequent microbore RP-HPLC peptide mapping in combination with MALDI-TOF MS and automated Edman degradation of this latter protein revealed 2 peptides of 11 and 18 amino acids. From this sequence information degenerate PCR primers were designed and synthesized.

With a PCR protocol a 51 bp (base pair) fragment was amplified within the longer peptide, From this sequence a homologous primer was synthesized and used in a second RT-PCR (reverse transcriptase-PCR) to amplify a 597 bp fragment.

This cDNA fragment was radioactively labeled and used for the screening of two positive pools from a chicken expression library in order to isolate the full length cDNA coding for β,β-carotene 15,15' enzyme.

The positive pools were obtained from a cDNA library from chicken duodenum which was screened for β,β-carotene 15,15' enzyme activity in a cellular transactivation assay. By this strategy several positive cDNA pools were identified. By combining the two strategies the gene coding for β,β-carotene 15,15' enzyme could be successfully cloned.

It is an object of the present invention to provide a protein having the vitamin A producing activity of β,β-carotene 15,15' enzyme comprising an amino acid sequence which is identical or homologous to SEQ ID NO: 1 (shown in FIG. 4) whereby the degree of homology to SEQ ID NO: 1 is at least 60%.

With the sequence of β,β-carotene 15,15' enzyme isolated from chicken, corresponding proteins from different animals like swine, cow, goat, dog, rabbit, poultry, fish and humans can easily be obtained. Since the chicken sequence is known, suitable regions of the nucleic acid sequence can be selected as primers for a polymerase chain reaction with a suitable nucleic acid which allows an easy and rapid amplification of the gene coding for the protein.

The present invention includes therefore not only proteins having an amino acid sequence identical to the sequence given in SEQ ID NO: 1 but also such proteins which have an amino acid sequence homologous to the SEQ ID NO: 1. The degree of homology is, however, at least 60%, preferably 70%, more preferably 80%, such as for example, at least 90%. Homology as defined in the present invention means that when the amino acid sequences of two proteins are aligned at least the given percentage is identical. The alignment of the amino acids is performed with the help of a suitable computer program which is commercially available, in particular, the Wisconsin Sequence Analysis Package GCG (Genetics Computer Group, University Research Park, Madison), Version 9.1, 1997. The remainder of the amino acids may be different. A homology of 90% for example means that 90% of the amino acids of the protein are identical compared with the amino acid sequence given in SEQ D) NO: 1 whereas 10% of the amino acids may be different. The proteins of the present invention have, however, the biological activity of β,β-carotene 15,15' enzyme which is explained above in more detail. In the present invention, this protein may be derived from other sources, for example, from other mammmals, such as from humans.

As used herein, the terms "protein" and "polypeptide" are used interchangeably throughout. The terms "nucleic acid" and "polynucleotide" are likewise used interchangeably.

The term "nucleic acid" is intended to include, without limitation, DNA, RNA, cDNA, and mRNA. As used herein, the DNA may be genomic, synthetic, or semi-synthetic. Moreover, the nucleic acids of the present invention include single-stranded and double stranded molecules.

As used herein "derived from" means that the protein, polypeptide, and/or polynucleotide exists naturally in an organism, such as for example, a chicken. However, the polypeptides and polynucleotides of the present invention may be produced/obtained from any source. Thus, the present invention includes recombinant, synthetic and semi-synthetic proteins, polypeptides, and polynucleotides.

The compositions of the present invention are said to be "isolated," such as for example "isolated polypeptide," "isolated polynucleotide," etc. As used herein, the term "isolated" is intended to mean that the polypeptide or polynucleotide is purified or, at least partially purified as described, for example, in FIG. 1.

Another aspect of the present invention concerns nucleic acid sequences coding for a protein having the biological activity of β,β-carotene 15,15' enzyme. A nucleic acid sequence coding for the enzyme derived from chicken is shown in SEQ ID NO: 2 (see FIG. 3). The nucleic acid sequences of the present invention code for a protein of the present invention or a part thereof. Shorter nucleotide sequences suitable for PCR have a length of at least 20 bases, preferably at least 25 bases and most preferred at least 30 bases.

The nucleic acid sequences of the present invention can be used as primers for the specific amplification of a gene or part thereof coding for β,β-carotene 15,15' enzyme. Primers can also be used for the specific amplification of 5' non-translating or 3' nontranslating sequences of the cDNA described above. The nucleic acid sequences of β,β-carotene 15,15' enzyme cDNA can be used as a probe for the detection of the coding as well as for the noncoding regions or parts thereof. The nucleic acid sequences of the present invention can be used as antisense RNA probes for in situ hybridization.

It is especially preferred to use primers and probes having a part of the sequence given in SEQ ID NO: 2 as primers and/or probes in test kits which can be used for the amplification and/or detection of genes/mRNAs coding for β,β-carotene 15,15' enzyme by the polymerase chain reaction (PCR). The selection of suitable parts of the nucleic acid sequence can be performed by the person skilled in the art without difficulties. A nucleic acid sequence used as a primer or probe is usually selected from a region which is highly conserved within the protein. Conserved means that the nucleic acid sequences of such regions of proteins obtained from different species are very similar.

On the other hand the preferred nucleic acid sequence should not be present in other nucleic acid sequences which do not code for β,β-carotene 15,15' enzyme, because this might lead to false positive results. By aligning several sequences derived from different species such regions can easily be determined. Although the nucleic acid can be a ribonucleic acid it is more preferred to have deoxyribonucleic acid sequences.

One preferred use in diagnostics is the detection of the presence of β,β-carotene 15,15' enzyme in patients. There is variability in β-carotene cleavage potential among the human population. Humans with low β,β-carotene 15,15' enzyme levels (with e.g. mutations or polymorphisms in the gene for β,β-carotene 15,15' enzyme) could be identified and selected for vitamin A supplementation.

A diagnostic kit based on PCR can be designed to detect frequent mutations in the enzyme gene. Another diagnostic option is quantification of mRNA by RT-PCR. With this diagnostic tool differences in expression of β,β-carotene 15,15' enzyme in various tissues and in different species can be found.

Since the protein has been expressed and a method for purifying the protein is described in detail in the examples the person skilled in the art can use the protein or peptides derived from the amino acid sequences in order to generate antibodies which specifically react with the protein. It is either possible to produce polyclonal antibodies by immunizing laboratory animals, like rabbits, sheep or goats preferably with an adjuvant or monoclonal antibodies by the well-known technique described by Köhler and Milstein (European Journal of Immunology, 1976, 6 (7), p. 511–519). The antibodies should specifically react with β,β-carotene 15,15' enzyme in order to avoid an unspecific crossreaction. This means that the antibodies of the present invention should preferably react with an epitope which is present only on a protein of the present invention.

Such antibodies can be preferably used in immunoassays for the detection and/or quantification of β,β-carotene 15,15' enzyme in a test fluid. The test fluid may be a liquid, like serum, obtained from a patient. There are several types of immunoassays which are well-known to the person skilled in the art. Very frequently one antibody, preferably a monoclonal antibody is fixed to a solid phase. This antibody is then brought into contact with the fluid containing the β,β-carotene 15,15' enzyme and after washing it is further reacted with a second monoclonal antibody which binds to another epitope of the enzyme. The second antibody is usually labeled and shows the presence of the sandwich consisting of the antigen and two different antibodies.

The antibodies can also be used in laboratory methods like Western blots or immuno-precipitations. Preferably such antibodies can be used in immunohistochemistry to detect epitopes of β,β-carotene 15,15' enzyme in embedded or fixed tissues or cells of any species of interest.

In a further embodiment of the present invention the β,β-carotene 15,15' enzyme is used for the production of vitamin A whereby the enzyme cleaves enzymatically β-carotene into two molecules of retinal which will subsequently be reduced by retinol dehydrogenase to vitamin A. The β,β-carotene 15,15' enzyme can be used to enzymatically convert carotene which may be obtained from plant sources. A preferred source of β-carotene is the alga *Dunaliella bardawil* which has a high endogenous level of β-carotene. Suitable algae can be grown conveniently and β-carotene can be purified therefrom at rather low cost. The carotene can be conveniently cleaved enzymatically by using a protein of the present invention. The carotene enzyme can preferably be immobilized in order to provide a continuous process.

Another aspect of the present invention concerns the introduction of the gene coding for a protein having β,β-carotene 15,15' enzyme activity into a suitable host cell. The first step in such a method is usually to insert the cDNA into a suitable vector. The vector must fit with the host dell into which the gene should be introduced. There are specific vectors available for bacteria, yeasts, plant cells, insect cells or mammalian cells. Preferably the gene is combined with genetic structures which provide the required genetic regulation like promotors, enhancers, ribosomal binding sites etc.

Systems for the expression of genes encoding carotenoid biosynthetic enzymes in procaryotes, especially in *E. coli* or *Bacillus subtilis* or Flavobacter and eucaryotes, e.g. fungi are known in the art and described e.g. in EP Publication Nos. 747 483 or EP 872 554.

The vector having the gene and the other required genetic structures is then introduced into suitable host cells by well-known methods like transformation, transfection, electroporation or microprojectile bombardment. Depending on the host cell it may be preferred to stably integrate the gene coding for a protein of the present invention into the genome of the host cell. The cells obtained by such methods can then be further propagated and if the cell is a plant cell it is possible to generate therefrom transgenic plants.

In one embodiment of the present invention the host cells are plant cells and tomato cells are especially preferred. The technology to produce transgenic tomatoes is well-established and the tomato contains sufficient β-carotene in order to come up with a reasonable vitamin A level after introduction of carotene enzyme into the tomato plant. In green pepper, melon or especially carrot the endogenous level of β-carotene is even higher and therefore also these plants are especially preferred.

Another preferred embodiment of the present invention concerns algae. Halotolerant algae may contain high levels of β-carotene. A transfection of such algae with an expression vector comprising the β,β-carotene 15,15' enzyme cDNA leads to a high intracellular vitamin A level which can easily be recovered from such algae by simple purification steps.

In another aspect of the present invention a gene coding for a protein of the present invention can be introduced into mammalian cells and especially into human cells. It is for example possible to insert the gene coding for a β,β-carotene 15,15' enzyme into suitable cells, for example peripheral blood stem cells. Such cells which contain the gene for β,β-carotene 15,15' enzyme may be administered to people having mutations or deletions in the β,β-carotene 15,15' enzyme gene. Such mutations and deletions, respectively, may have the effect that such patients are not able to cleave β-carotene enzymatically. Therefore, such patients always have a low vitamin A level and thus suffer from various developmental and ophthalmological problems. The administration of suitably transfected cells expressing the β,β-carotene 15,15' enzyme to such patients by way of somatic gene therapy is a way to improve their situation.

The following examples are provided to further illustrate methods of preparation of the enzyme of the present invention, as well as certain physical properties and uses thereof. These examples are illustrative only and are not intended to limit the scope of the invention in any way.

EXAMPLES

Example 1

Assay of β,β-carotene 15.15' Enzyme Activity

For the tests the following solutions were prepared:

a. Solution 1 (mixed micelle solution): Glycocholic acid (1.16 g) was dissolved in 5 ml $H_2O$ under stirring and by drop-wise addition of 5 N NaOH. After the pH was adjusted to 6.8–7.2 with acetic acid and the volume increased to 10 ml with $H_2O$, 80 mg of asolectin (Fluka) were added and dissolved under stirring.

b. Solution 2 (substrate solution): 500 µl of an α-tocopherol solution (10 mg/ml in hexane) and 235 µg of a β-carotene solution (80 µg/ml of pure all-E-β-carotene in benzene) were mixed in a glass vial, protected from light and the solvents evaporated under a gentle nitrogen stream. 1 ml of solution 1 was added under vortexing and eventually a few short ultrasonic bursts until a clear solution occurred.

c. Solution 3 (homogenization buffer): 100 mM $KH_2PO_4$ adjusted with 5 N KOH to pH 7.8 and containing 4 mM $MgCl_2$, $6H_2O$ and 30 mM nicotinarnide.

d. Solution 4 (GSH solution): 60 mg/ml reduced glutathione dissolved in solution 3.

e. Solution 5 (standard solution): 10 µg/ml vitamin A acetate in hexane/chloroform 9:1.

Activity Assay 2 ml of the enzyme preparation (approximately 4 mg protein, assayed by BCA protein assay, Pierce Chemicals) were placed in a light-protected glass vial in a shaking water bath (30 minutes, 37° C.). 0.2 ml of solution 4 was added and the reaction was started after 2 minutes of temperature equilibration by addition of 50 µl of solution 2. After 3 hours, the reaction was stopped by placing the vials on ice and subsequent addition of 1 ml acetonitrile followed by 5 ml chloroform. The vials were vortexed 3 times for 7 seconds and phase separation was obtained by centrifugation for 5 minutes at 5000 g. Extraction was repeated twice with 0.6 ml chloroform. The combined chloroform phases were evaporated and resolubilized in 200 µl solution 5 under short sonication. Insoluble material was removed by filtration through 0.45 µm filters. An aliquot of 20 µl was separated by HPLC on a reversed phase $C_{18}$ column (Lichrospher 100, 5 µm, 12.5 cm×4.6 mm, Bischoff Chromatography, Leonberg, Germany; 1 ml/min, column temperature 25° C.) with a discontinuous, optimized gradient of acetonitrile/tetrahydrofuran/(1% ammonium acetate in $H_2O$) from 50:20:30 (eluent A) to 50:44:6 (eluent B). These conditions allow complete separation of β,β-carotene and retinal as well as apo-β-carotenals and retinoic acids. Calibration curves were made for both β,β-carotene and retinal in the concentration ranges 2–40 ng/µl and 1–10 ng/µl, respectively, and were correlated to the value of vitamin A acetate which served as an internal standard. Enzymatic activity was expressed as the amount of retinal liberated in the activity assay during 3 hours of incubation at 37° C. (100%=17.6 nmol).

Example 2

Purification of β,β-carotene 15,15' Enzyme

Purification was done as rapidly as possible, and all buffers and equipment were cooled to 4° C.

Solution 6 (protease inhibitor-containing homogenization buffer): 125 mM benzamidine HCl, 250 mM 6-aminocaproic acid and 125 µM soybean trypsin inhibitor were dissolved in $H_2O$ by sonication. A 4 ml-aliquot of this solution was mixed with 100 ml of solution 3.

Solution 7: 10 mM $KH_2PO_4$, 1 mM reduced glutathione, pH 7.8.

Solution 8 (eluent A, phenyl-Sepharose chromatography): 10 mM $KH_2PO_4$, 1 mM reduced glutathione, 0.5 M $(NH_4)_2SO_4$, pH 7.8.

Solution 9 (eluent B, phenyl-Sepharose chromatography): 10 mM $KH_2PO_4$, 1 mM reduced glutathione, 10% glycerol, pH 7.8.

Solution 10 (eluent B, Poros HQ chromatography): 10 mM $KH_2PO_4$, 1 mM reduced glutathione, 0.5 M NaCl, 10% glycerol, pH 7.8.

Solution 11 (elution buffer for gel permeation chromatography): 50 mM $KH_2PO_4$, 1 mM reduced glutathione, 150 mM NaCl, 10% glycerol, pH 7.8.

Laying hens at an age of 20–24 weeks (strain Lohmann LSL, Hatchery Wuethrich, CH-3123 Belp, Switzerland) were kept on a pigment-free chicken diet (Kliba 3179,Kliba, CH-4303 Kaiseraugst, Switzerland). The animals were killed by decapitation and the first 20 cm of the duodenal loop was removed, separated from pancreas and rinsed with 40 ml each of 0,9% NaCl solution. The intestines (duodenal loops) were immediately frozen in dry ice and stored at −80° C. until use.

Ten intestines (duodenal loops) were thawed on ice in approximately 2 hours and opened length-wise in an ice cooled Petri dish. The mucosa was scraped off with a slide, weighed and homogenized in a Teflon-glass Potter-Elvehjem homogenizer in 4 volumes of solution 6 with six strokes. Upon centrifugation at 62000 g for 1 hour, the clear supernatant was divided into 32 aliquots of 15 ml each. From these preparations an The precipitate obtained from the 20–45% step was centrifugated at 5000 g for 10 minutes and the pellet was stored at −80° C. for further use.

Ten aliquots of the $(NH_4)_2SO_4$ pellet were dissolved in 150 ml of solution 7, sterile-filtered and loaded on a HiLoad 26/10 phenyl-Separise High Performance column (column volume 53 ml; Pharmacia, Uppsala, Sweden) and equilibrated with solution 8. Proteins were eluted at a flow rate of 8 ml/minute with a steep gradient over 1 column volume (CV) from solution 8 to solution 9. β,β-Carotene 15,15' enzyme eluted at a conductivity of <15 mS/cm, but only fractions with a conductivity of <1 mS/cm were pooled and directly loaded onto a 30 ml Blue Sepharose 6 Fast Flow column (Pharmacia) equilibrated with solution 9. β,β-Carotene 15,15' enzyme activity eluted (at a flow rate of 8 ml/min) in the break-through fractions which were (again) directly loaded onto a 20 ml Poros HQ/M anion exchange chromatography column (PerSeptive Biosystems, Framingham, MA, USA) equilibrated with solution 9. β,β-Carotene 15,15' enzyme was eluted at a flow rate of 15 ml/minute with a linear gradient over 18 CV from solution 9 to solution 10. Activity was detected in the gradient in a conductivity range of 10–20 mS/cm. The pooled fractions (70 ml) were concentrated to 1.3 ml with Ultrafree-15 filter units (MW cut-off 50,000; Millipore, Bedford, Mass., USA). An aliquot of the concentrate (500 µl) was loaded onto a Superdex 200 HR 10/30 gel filtration column (CV 24 ml; Pharmacia) and eluted at a flow rate of 0.5 ml/minute with solution 11. Aliquots of each fraction were used for activity assays (see example 1) and, upon concentration, for SDS-PAGE (with MOPS running buffer) on 10% NUPAGE gels (Novex, San Diego, Calif., USA). The results of this experiment are shown FIG. 1 and Table 1.

TABLE 1

| Purification step | Total protein (mg) | Total activity (nmol/h) | Yield (%) | Specific activity (pmol/(h · mg)) | Purification factor |
|---|---|---|---|---|---|
| $(NH_4)_2SO_4$ pellet | 779 | 8.61 | 100 | 11.0 | — |
| phenyl-Sepharose | 80.8 | 8.27 | 96.1 | 102 | 9.27 |
| Blue Sepharose | 16.0 | 8.86 | 103 | 554 | 50.1 |
| Poros HQ | 1.56 | 3.90 | 45.3 | 2500 | 226 |

Table 1:
Summary table for the purification of β,β-carotene 15,15' enzyme starting with 10 aliquots of the $(NH_4)_2SO_4$ pellet (means of 3–4 measurements).

Example 3

Amino Acid Sequence Information for β,β-carotene 15,15' Enzyme

For amino acid sequence analysis, fractions of the gel filtration run (as shown in FIG. 1) were separated on a 8–16% Tris/glycine gel (Novex), and the proteins transferred to an Immobilon pSQ membrane (Millipore) and stained with amido black.

Since protein A proved to be N-terminally blocked, multiple aliquots of fraction 18 from the gel filtration run (see FIG. 1) were separated on a 10% Tris/glycine gel (Novex), and the gel was stained with Colloidal Coomassie Blue (Novex). The band corresponding to protein A was excised from the gel, and the protein digested in-gel with trypsin. The tryptic digest was separated by micro-bore reversed-phase HPLC on a 150×1.0 mm Vydac C18 column (Vydac, Hesperia, Calif., USA). Peptides were eluted with an acetonitrile gradient in 0.1% trifluoroacetic acid, and peptide containing fractions were collected for further analysis. Two fractions were identified by MALDI-TOF-MS (Voyager Elite, PerSeptive Biosystems) to contain one single peptide each. N-terminal Edman degradation revealed the following sequences:
(1) Ala-Glu-Val-Gln-Gly-Gln-Leu-Pro (Seq. ID No. 3)
(2) Asn-Lys-Glu-Glu-His-Pro-Glu-Pro-Ile-Lys-Ala-Glu-Val-Gln-Gly-Gln-Leu-Pro (Seq. ID No. 6)

Note that the last 8 amino acids of peptide (2) correspond to peptide (1).

Example 4

Cloning the Full Length cDNA for the β,β-carotene 15,15' Enzyme

A) RNA isolation:

A 4 week old Vedette chicken was killed, the duodenum was removed, washed with sterile PBS and cut open with scissors. The mucosal layer was scraped off with a glass slide, weighed and homogenized immediately with a Polytron in 1 ml of Trizole reagent (Life Technologies) per 100 mg of tissue. Then the standard protocol from Life Technologies was followed. Poly A mRNA was isolated by the polyATtract mRNA Isolation kit from Promega Corporation, Madison.

B) PCR and RT-PCR:

In the peptide sequence NKEEHPEPIKAEVQGQLP (peptide 2 of Example 3) (Seq. ID No. 7) two degenerate primers were designed: In order to have a lower degeneracy the base Inosin was used in one and in two wobble positions, respectively.

5' primer: 5'AAC AAR GAR GAS CAY CCI GA3' (Seq. ID No. 8) (20 mer with a degeneracy of 16×)

3' primer: 5'SAG CTG ICC CTG LAC YTC SGC3' (Seq. ID No. 9) (21 mer with a degeneracy of 8×)

R=A or G, S=C or G, Y=C or T

The oligos were synthesized on a Pharmacia Gene Assembler Plus using standard phosphoramnidite chemistry. Deprotection was done with 1 ml conc. ammonium hydroxide solution (Applied Biosystems) and final desalting was performed with a NAP 10 column (Amersham Pharmacia Biotech).

For PCR 100 ng of chicken duodenal cDNA were taken as template and the following steps performed: 94° C. 30"; 52° C. 30"; 72° C. 1' for 40 cycles. The resulting of 51 bp was cut out from a 10% polyacrylarnide gel, electroeluted on DEAE paper at 300 V for 1.5 hours, eluted from the DEAE paper once with 40 µl and twice with 30 µl 1.5 M NaCl, 5 mM Tris, 0.5 mM EDTA, precipitated with 2.5 volumes of ethanol 100% and 1 µg glycogen, washed with 0.5 ml of 80% ethanol, dried and dissolved in 20 µl TE (10 mM Tris, 1 mM EDTA).

The resulting fragment of 51 bp was cloned into pGEM-T Easy, a commercially available T/A cloning vector (Promega Corporation, Madison). The corresponding cDNA sequence was determined by automated fluorescent sequencing on a Vistra DNA Sequencer 725 (Amersham Pharmacia Biotech).

From the above DNA sequence a homologous forward primer was derived: 5'TCT GAATTCCGGAGCCCATAAAAGC3' (primer dioxyl2) (Seq. ED No. 10)

At the 5' end an EcoRI site (underlined sequence) was introduced; the following 17 nucleotides are homologous to the previously obtained enzyme sequence.

In a RT-PCR reaction a polyT/Not primer (commercially available from Invitrogen, San Diego) was used as reverse primer together with primer dioxyl 12.

One tube RT-PCR kit from Boehringer Mannheim was taken and the corresponding protocol followed:

| mix 1: | |
|---|---|
| 18.3 µl | H$_2$O |
| 2.5 µl | DTT (100 mM) |
| 1.0 µl | dNTPs (10 mM) |
| 1.0 µl | oligo dT/Not (0.2 µg/µl) (3' primer) |
| 1.0 µl | dioxyl2 (5' primer) (20 µM) |
| 0.2 µl | RNAse inhibitor (40 U/µl) |
| 1.0 µl | chicken duodenal total RNA (2.2 µg/µl) |
| 25.0 µl | |

| mix 2: | |
|---|---|
| 14.0 µl | H$_2$O |
| 10.0 µl | RT-PCR buffer 5× |
| 1.0 µl | enzyme mix (AMV RT, Taq and Pwo DNA Polymerase) |
| 25.0 µl | |

The 2 mixes were combined and the PCR protocol started on a MJ Research PTC200 DNA Engine.
50° C. 30"
94° C. 2'
94° C. 30"
57° C. 30" 10 cycles
68° C. 45"
94° C. 30"
62° C. 30" 25 cycles
68° C. 45"+3"/cycle
68° C. 7'
4° C. over night With this RT-PCR protocol a band of 597 bp was amplified from chicken total duodenal RNA. The PCR band was isolated from a 1% agarose gel, cloned into pGEM-T Easy cloning vector and subsequently sequenced. The original peptide is present in the sequence as well as an open reading frame over the whole sequence of 597 bp.

C) Chicken cDNA-library:

From chicken duodenal polyA$^+$ RNA cDNA was made with the Copy Kit (Invitrogen, San Diego) using a modified Gubler-Hoffman procedure. The cDNA was size-selected (0.9–5.5 kb) and cloned into the eukaryotic expression vector pcDNA1.1/Amp (Invitrogen).

Electroporation into E. coli Top 10 was done with a Bio-Rad Gene Pulser II system following the standard protocol. This resulted in a cDNA library of 480,000 individual clones. The library was split into 250 pools with 1500–2500 individual clones each. Each pool was amplified in 100 ml LB medium: Bacterial growth was stopped at OD 0.8–1.0 by adding chloramphenicol to a final concentration of 170 µg/ml. Incubation was continued over night in order to increase the DNA amount.

Figure 2:
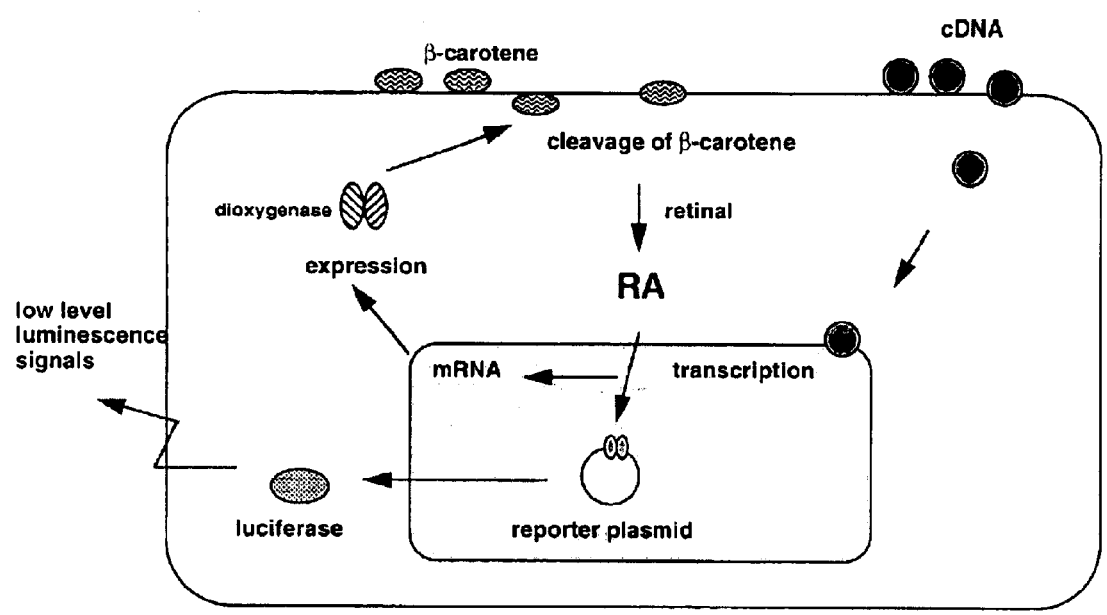
FIG. 2 shows schematically the transactivation assay in eukaryotic cells. cDNAs are transfected and expressed in MCF-7 cells. When incubated with β-carotene, a positive pool shows cleavage activity. The cleavage product retinal is further oxidized to retinoic acid (RA) which binds to the endogenous receptor. The receptor/ligand complex binds to the response element on the reporter plasmid and leads to an enhanced transcription of the luciferase gene. The luminescene signals are detected in a luciferase assay with a sensitive CCD camera.

D) Activity screening of the chicken cDNA library:

90 of the above pools were tested for activity in a transactivation assay based on the detection of retinoic acid which is produced in eukaryotic cells after β-carotene cleavage. The principle of the activity test is shown in FIG. 2.

5 µg of DNA from each pool were transfected with 20 µg of lipofectin (Life Technologies) into a reporter cell line bearing a luciferase reporter plasmid with a RARE (retinoic acid response element) in front of the tk promoter (Herpes simplex thymidine kinase promoter). Transfections were done for 7 hours under serum free conditions. After 7 hours the transfection mix was removed and RPMI medium with 10% charcoal treated FCS (fetal calf serum) was added. After 20 hours of incubation β-carotene (β-carotene 10% CWS, F. Hoffmann-La Roche Ltd.) or a placebo formulation were added to the culture medium to a final β-Carotene concentration of 5 µM. Incubation was continued for 18 hours. Then cells were washed with PBS, and luciferase expression was measured after substrate addition with a nitrogen cooled slow scan CCD camera (AstroCam Ltd.) Exposure time usually was 8 min. Analysis was done with the Image Pro Plus 3.0 software package (Media Cybematic, Maryland). 3 pools were strongly positive, 7 pools showed weaker, but detectable activity.

One of the positive pools was plated on a square agar plate. 2 filters (nylon membranes, Gene Screen, NEN Research Products, Boston) were processed and screened with the radioactively (($\alpha^{32}$P) dATP, Amersham) labeled 597 bp PCR-fragment. From 9500 colonies screened, 14 were double positive. From 36 colonies picked, 5 showed the same pattern after restriction site analysis. 2 clones were sequenced from the 5' end and the original 51 bp sequence was found. Subsequently the whole cDNA was sequenced and confirmed twice.

All molecular biological procedures were done according to Sambrook, Fritsch and Maniatis, Laboratory Manual, Cold Spring Harbor Laboratory Press (1989), which is incorporated by reference as if recited in full herein, if not otherwise mentioned.

The obtained cDNA sequence is shown in FIG. 3 and the amino acid sequence deduced therefrom in FIG. 4.

FIG. 4 shows the derived amino acid sequence having 526 residues.

Example 5

Sequence Comparison

By sequence comparison with the EMBL Genbank a high homology between the known protein RPE65 (Hamel et al., J.Biol.Chem. (1993) p. 15751–15757) and the β,β-carotene 15,15' enzyme was found. A homology of 55.5% on the amino acid level was found. The sequence alignment is shown in FIG. 5.

Example 6

Expression of the cDNA for β-β-carotene 15,15' Enzyme in *E. coli*

With PCR the coding sequence of the β-β-carotene 15,15' enzyme cDNA was amplified and the resulting fragment of 1578 bp was cloned into the EcoRI/BamHI site of the prokaryotic expression vector pQE-12 (Qiagen). The vector contains an in frame hexa-His affinity tag at the C-terminus of the enzyme. In addition, this plasmid contains a regulated promoter with two lacI repressor binding sites.

The *E. Coli* strain M15pREP4 was transformed with the expression plasmid. For expression 1l LB medium, containing 100 μg/ml ampicillin and 25 μg/ml kanamycin, was inoculated with 30 ml of an overnight culture. Growth was allowed until $OD_{600}$ of 0.6–0.8 was reached. At this point the culture was induced with 1 mM IPTG (isopropyl-β-thiogalactoside) and growth continued for another 1.5–2 hours. Bacteria were harvested by centrifugation and the pellet was frozen at −80° C.

The pellet was thawed by stirring in 20 ml extraction buffer (300 mM NaCl, 50 mM $NaH_2PO_4$, 20mM Tris-HCl, 1 mg/ml Tween 40; pH 7.8) including 2.5 mg/ml dodecyl-β-D-maltoside. 1 ml protease inhibitor cocktail (5.9 mM benzarnidine-HCl, 10 mM 6-aminoaproic acid, 5 μM soybean trypsin inhibitor) was added at the same time.

The bacterial cells were lysed by a 4 minute treatment with a Polytron (Kinematica AG, Switzerland) using a PT7 unit following a 4 minute sonication with a Branson Sonifier 250.

The lysate was spun at 12000×g and the supernatant purified over a $Co^{2+}$-chelate column (Talon Superflow Resin, Clontech, Heidelburg, Germany). The protein was eluted with 15–20 ml of extraction buffer containing 150 mM imidazole.

The fractions were loaded on a 10% polyacrylamide gel and the protein containing fractions dialyzed against 150 mM tricine, 5 mM $FeSO_4$, 3 mg/ml reduced glutathione, 0.21 mg/ml sodium cholate. The gel is shown in FIG. 6. The samples were then assayed in the enzyme activity assay.

Example 7

Expression of Recombinant β-β-carotene 15,15' Enzyme in the Human Duodenal Cell Line HuTu80

With PCR the coding sequence of the β-β-carotene 15,15' enzyme cDNA was amplified and the resulting fragment of 1578 bp was cloned into the BamHI/XhoI site of the plasmid $pSFV_2gen$. This vector is part of the Semliki Forest Virus expression system, which works highly efficiently in most mammalian cells.

The plasmid was used for in vitro synthesis of recombinant RNA, which was subsequently electroporated together with a helper virus into BHK cells (baby hamster kidney cells) for production of a high titer virus stock. With an aliquot of this stock the human duodenal cell line HuTu80 was infected. 6–18 hours after infection the cells were harvested and the pellet frozen at −80° C. Either the whole cell pellet, the cytoplasmic fraction or the membrane fraction was used in an activity assay. β-β-carotene 15,15' enzyme activity was found in the whole cell extract and in cytosolic fractions, while in the membrane fraction no activity was detected.

Example 8

β-β-carotene 15,15' Enzyme Activity of the Recombinant Protein Expressed in *E. coli* and in Human Cells After expression in *E. coli* and purification over a metal chelate column, the protein shows cleavage activity with β-carotene as substrate. Retinal was the only product detected by HPLC after incubation with β-carotene. No apocarotenals or other metabolites were found. This was proved by HPLC analysis as shown in FIGS. 7 and 8.

SEQUENCE LISTING

<160> NUMBER OF SEQ ID NOS: 10

<210> SEQ ID NO 1
<211> LENGTH: 526
<212> TYPE: PRT
<213> ORGANISM: CHICKEN

<400> SEQUENCE: 1

Met Glu Thr Ile Phe Asn Arg Asn Lys Glu Glu His Pro Glu Pro Ile
 1               5                  10                  15

Lys Ala Glu Val Gln Gly Gln Leu Pro Thr Trp Leu Gln Gly Val Leu
            20                  25                  30

Leu Arg Asn Gly Pro Gly Met His Thr Ile Gly Asp Thr Lys Tyr Asn
        35                  40                  45

-continued

```
His Trp Phe Asp Gly Leu Ala Leu Leu His Ser Phe Thr Phe Lys Asn
     50                  55                  60
Gly Glu Val Tyr Tyr Arg Ser Lys Tyr Leu Arg Ser Asp Thr Tyr Asn
 65                  70                  75                  80
Cys Asn Ile Glu Ala Asn Arg Ile Val Val Ser Glu Phe Gly Thr Met
                 85                  90                  95
Ala Tyr Pro Asp Pro Cys Lys Asn Ile Phe Ala Lys Ala Phe Ser Tyr
             100                 105                 110
Leu Ser His Thr Ile Pro Glu Phe Thr Asp Asn Cys Leu Ile Asn Ile
             115                 120                 125
Met Lys Thr Gly Asp Asp Tyr Ala Thr Ser Glu Thr Asn Phe Ile
 130                 135                 140
Arg Lys Ile Asp Pro Gln Thr Leu Glu Thr Leu Asp Lys Val Asp Tyr
145                 150                 155                 160
Ser Lys Tyr Val Ala Val Asn Leu Ala Thr Ser His Pro His Tyr Asp
                 165                 170                 175
Ser Ala Gly Asn Ile Leu Asn Met Gly Thr Ser Ile Val Asp Lys Gly
             180                 185                 190
Arg Thr Lys Tyr Val Leu Phe Lys Ile Pro Ser Ser Val Pro Glu Lys
             195                 200                 205
Glu Lys Lys Lys Ser Cys Phe Lys His Leu Glu Val Val Cys Ser Ile
210                 215                 220
Pro Ser Arg Ser Leu Leu Gln Pro Ser Tyr Tyr His Ser Phe Gly Ile
225                 230                 235                 240
Thr Glu Asn Tyr Ile Val Phe Ile Glu Gln Pro Phe Lys Leu Asp Ile
                 245                 250                 255
Val Lys Leu Ala Thr Ala Tyr Ile Arg Gly Val Asn Trp Ala Ser Cys
             260                 265                 270
Leu Ser Phe His Lys Glu Asp Lys Thr Trp Phe His Phe Val Asp Arg
             275                 280                 285
Lys Thr Lys Lys Glu Val Ser Thr Lys Phe Tyr Thr Asp Ala Leu Val
 290                 295                 300
Leu Tyr His His Ile Asn Ala Tyr Glu Glu Asp Gly His Val Val Phe
305                 310                 315                 320
Asp Ile Val Ala Tyr Arg Asp Asn Ser Leu Tyr Asp Met Phe Tyr Leu
                 325                 330                 335
Lys Lys Leu Asp Lys Asp Phe Glu Val Asn Asn Lys Leu Thr Ser Ile
             340                 345                 350
Pro Thr Cys Lys Arg Phe Val Val Pro Leu Gln Tyr Asp Lys Asp Ala
             355                 360                 365
Glu Val Gly Ser Asn Leu Val Lys Leu Pro Thr Ser Ala Thr Ala Val
             370                 375                 380
Lys Glu Lys Asp Gly Ser Ile Tyr Cys Gln Pro Glu Ile Leu Cys Glu
385                 390                 395                 400
Gly Ile Glu Leu Pro Arg Val Asn Tyr Asp Tyr Asn Gly Lys Lys Tyr
                 405                 410                 415
Lys Tyr Val Tyr Ala Thr Glu Val Gln Trp Ser Pro Val Pro Thr Lys
             420                 425                 430
Ile Ala Lys Leu Asn Val Gln Thr Lys Glu Val Leu His Trp Gly Glu
             435                 440                 445
Asp His Cys Trp Pro Ser Glu Pro Ile Phe Val Pro Ser Pro Asp Ala
 450                 455                 460
```

| | | | | | | | | | | | |
|---|---|---|---|---|---|---|---|---|---|---|---|
| Arg | Glu | Glu | Asp | Glu | Gly | Val | Val | Leu | Thr | Cys | Val | Val | Val | Ser | Glu |
| 465 | | | | 470 | | | | | 475 | | | | | 480 |

Pro Asn Lys Ala Pro Phe Leu Leu Ile Leu Asp Ala Lys Thr Phe Lys
                   485                     490                   495

Glu Leu Gly Arg Ala Thr Val Asn Val Glu Met His Leu Asp Leu His
        500                     505                     510

Gly Met Phe Ile Pro Gln Asn Asp Leu Gly Ala Glu Thr Glu
        515                     520                   525

<210> SEQ ID NO 2
<211> LENGTH: 3111
<212> TYPE: DNA
<213> ORGANISM: CHICKEN

<400> SEQUENCE: 2

```
cggatccact agtaacggcc gccagtgtgg tggaatccat ccttctatgt aacaggaaag     60
agctgttctt agcccagaga ggagggcacc gtacgcctgc aggagcagct gggtagagga    120
cacaggagag cgatggagac aatatttaac agaaacaaag aagagcatcc agagcccata    180
aaagctgagt gcaaggtcag ttgcccact tggttgcaag ggtacttct ccgaaatggc     240
ccagggatgc acacaatagg ggacactaaa tacaaccact ggtttgatgg cttggctctg    300
ctgcacagct tcacgtttaa aaatggtgaa gtttactaca gaagtaagta cctccgaagt    360
gacacataca actgcaatat agaagcaaac cgaatcgtgg tgtctgagtt tggaaccatg    420
gcttatccgg atccatgcaa aaacatattt gccaaggcat tctcatactt atctcacacc    480
attcctgagt tcacggacaa ctgcctgatc aacattatga aaactgggga tgattattat    540
gctaccagtg agactaactt catcagaaaa attgatccac agactctgga gacactagat    600
aaggtagact acagcaaata tgtagctgta aacttggcaa cttctcaccc acactatgac    660
agtgctggaa atattctcaa catgggtact tcaattgttg ataaagggag aacaaaatat    720
gttctcttta agatcccttc ctctgtacca gaaaagaaa agaagaaatc ttgttttaaa    780
cacctggaag tagtatgctc catcccttct cgctccctgc tccaaccaag ctactaccac    840
agctttggaa tcacagaaaa ttatattgtg ttcatagagc agccatttaa actggatatt    900
gtcaaactgg caactgccta catccgaggt gtgaactggg cttcctgcct ttcctttcat    960
aaggaggata agacgtggtt tcactttgta gacagaaaga cgaaaaaaga agtatccacc   1020
aagttttaca ctgatgcttt ggtgctttat caccacataa atgcttacga agaagatggc   1080
cacgttgttt ttgatatcgt tgcctacaga gacaatagct tgtacgatat gttttactta   1140
aaaaaactgg acaaagactt tgaagtgaac aacaagctta cctccatccc aacctgcaag   1200
cgctttgttg tgcctctgca gtatgacaag gatgcagaag taggttctaa tttagtcaaa   1260
cttccaactt ccgcaactgc tgtaaaagaa aaagatggca gcatctattg tcaacctgaa   1320
atattatgtg aagggataga actgcctcgt gtcaactatg actacaatgg caaaaaatac   1380
aagtatgtct atgcaacaga agtccagtgg agcccagttc ctacaaagat tgcaaaactg   1440
aatgtccaaa caaggaagt actgcactgg ggagaagacc actgctggcc ctcagagccc   1500
atctttgttc ccagccccga tgcaagagaa gaggatgaag gtgttgtttt gacctgtgtt   1560
gtggtgtctg agccaaataa agcacccttc ctactcatct ggatgctaa acattcaaa    1620
gaattgggcc gagccacagt taacgtagaa atgcatctgg acctgcatgg gatgtttata   1680
ccacagaatg atttggggc tgagacggaa taaaacgcta ttgatccgac tacacaaact   1740
gagacaactt tctactgaac atgagttaat atccctttta ccattcaaga acaaccatat   1800
```

-continued

```
aacgacacaa aatgactatg tataatctct taaataatag atataatcct tttaaggcac    1860
agcgatgagt tttactacag gtaacgatat gcacaactgg catataacta ttccaaaaga    1920
agaagaacga tcagtgtttt agaagtgcta atgttgtaca taacggcggc agagggaaca    1980
ggagagaaag gtaacgggaa tatttaatag aatatagatt tctgagcaaa tgaagtgcag    2040
tatttatggt gtgatgcatg gcatgagtca cataggtctg cagctcatgt atcttttaga    2100
gatcgtttca agattgcagc ttgtgatgca agttttctcc agccagaaaa cctcatttta    2160
aaccatctgc tactggtaat tcataccaat gcattttctt ggtgctcgat ttacactata    2220
accaaagtta agtattacat tcaggtgcta caactttcta atttacaacc gaaacaaaca    2280
agcaaacagc acttgctttg ctaataaccc catggtgtat ttttcctttt tatgatgaca    2340
aaaccaagta catatggttt tatgtagcat tcaattatac ttcagtgcta ttccatccta    2400
atgttataag caatttgtat ttaaatcagt tttccttgag aatatctgac ataacatttt    2460
gtgtaatgag atgactatgt tgtctaaaga tgaacaggaa tgtatctttt attagtattg    2520
ttaattgtgt tactaatact atgcatatga atgagagcaa tgtatttcta ggagaactca    2580
gatatacatt caacaatttc tgtaggtgaa aatgcattta ctgatgaaag ttgaatcgtt    2640
aatgagggag aaaactgggt atccatccat ccaactatgt taggtgttca cctggtctgt    2700
atgtgacacc acgctgtttg ggtatctctc actttcacat acctgttctc atggtttctg    2760
ctactcactg tattttgcag gagagaaaca aaatgaaatc actgtcactt actatcgccc    2820
catcacataa gaacaatggg gctttggtga cttgttcatg attacataag atgtttgcag    2880
cagagcagca atagaaccaa caccatccac agttcttgct tgctctgtta tgactccctt    2940
tgctgtcttt atggtttgca tgtatgaaga atacactgcc taattctaat gttaaaaagt    3000
cactggggtc agatctagag cttaagtaag cagtctgggg ttttcaaatg tttatatgtt    3060
ccataaaatg gaaataaaca cctccataat aaaaaaaaaa aaaaaaaaaa a            3111
```

<210> SEQ ID NO 3
<211> LENGTH: 8
<212> TYPE: PRT
<213> ORGANISM: CHICKEN

<400> SEQUENCE: 3

```
Ala Glu Val Gln Gly Gln Leu Pro
 1               5
```

<210> SEQ ID NO 4
<211> LENGTH: 506
<212> TYPE: PRT
<213> ORGANISM: CHICKEN

<400> SEQUENCE: 4

```
Glu Glu His Pro Glu Pro Ile Lys Ala Glu Val Gln Gly Gln Leu Pro
 1               5                  10                  15

Thr Trp Leu Gln Gly Val Leu Leu Arg Asn Gly Pro Gly Met His Thr
                20                  25                  30

Ile Gly Asp Thr Lys Tyr Asn His Trp Phe Asp Gly Leu Ala Leu Leu
            35                  40                  45

His Ser Phe Thr Phe Lys Asn Gly Glu Val Tyr Tyr Arg Ser Lys Tyr
        50                  55                  60

Leu Arg Ser Asp Thr Tyr Asn Cys Asn Ile Glu Ala Asn Arg Ile Val
 65                  70                  75                  80
```

-continued

```
Val Ser Glu Phe Gly Thr Met Ala Tyr Pro Asp Pro Cys Lys Asn Ile
             85                  90                  95

Phe Ala Lys Ala Phe Ser Tyr Leu Ser His Thr Ile Pro Glu Phe Thr
            100                 105                 110

Asp Asn Cys Leu Ile Asn Ile Met Lys Thr Gly Asp Asp Tyr Tyr Ala
            115                 120                 125

Thr Ser Glu Thr Asn Phe Ile Arg Lys Ile Asp Pro Gln Thr Leu Glu
            130                 135                 140

Thr Leu Asp Lys Val Asp Tyr Ser Lys Tyr Val Ala Val Asn Leu Ala
145                 150                 155                 160

Thr Ser His Pro His Tyr Asp Ser Ala Gly Asn Ile Leu Asn Met Gly
                165                 170                 175

Thr Ser Ile Val Asp Lys Gly Arg Thr Lys Tyr Val Leu Phe Lys Ile
            180                 185                 190

Pro Ser Ser Val Pro Glu Lys Glu Lys Lys Ser Cys Phe Lys His
            195                 200                 205

Leu Glu Val Val Cys Ser Ile Pro Ser Arg Ser Leu Leu Gln Pro Ser
210                 215                 220

Tyr Tyr His Ser Phe Gly Ile Thr Glu Asn Tyr Ile Val Phe Ile Glu
225                 230                 235                 240

Gln Pro Phe Lys Leu Asp Ile Val Lys Leu Ala Thr Ala Tyr Ile Arg
            245                 250                 255

Gly Val Asn Trp Ala Ser Cys Leu Ser Phe His Lys Glu Asp Lys Thr
            260                 265                 270

Trp Phe His Phe Val Asp Arg Lys Thr Lys Glu Val Ser Thr Lys
            275                 280                 285

Phe Tyr Thr Asp Ala Leu Val Leu Tyr His His Ile Asn Ala Tyr Glu
            290                 295                 300

Glu Asp Gly His Val Val Phe Asp Ile Val Ala Tyr Arg Asp Asn Ser
305                 310                 315                 320

Leu Tyr Asp Met Phe Tyr Leu Lys Lys Leu Asp Lys Asp Phe Glu Val
            325                 330                 335

Asn Asn Lys Leu Thr Ser Ile Pro Thr Cys Lys Arg Phe Val Val Pro
            340                 345                 350

Leu Gln Tyr Asp Lys Asp Ala Glu Val Gly Ser Asn Leu Val Lys Leu
            355                 360                 365

Pro Thr Ser Ala Thr Ala Val Lys Glu Lys Asp Gly Ser Ile Tyr Cys
            370                 375                 380

Gln Pro Glu Ile Leu Cys Glu Gly Ile Glu Leu Pro Arg Val Asn Tyr
385                 390                 395                 400

Asp Tyr Asn Gly Lys Lys Tyr Lys Tyr Val Tyr Ala Thr Glu Val Gln
                405                 410                 415

Trp Ser Pro Val Pro Thr Lys Ile Ala Lys Leu Asn Val Gln Thr Lys
            420                 425                 430

Glu Val Leu His Trp Gly Glu Asp His Cys Trp Pro Ser Glu Pro Ile
            435                 440                 445

Phe Val Pro Ser Pro Asp Ala Arg Glu Glu Asp Glu Gly Val Val Leu
            450                 455                 460

Thr Cys Val Val Val Ser Glu Pro Asn Lys Ala Pro Phe Leu Leu Ile
465                 470                 475                 480
```

```
Leu Asp Ala Lys Thr Phe Lys Glu Leu Gly Arg Ala Thr Val Asn Val
                485                 490                 495

Glu Met His Leu Asp Leu His Gly Met Phe
            500                 505

<210> SEQ ID NO 5
<211> LENGTH: 529
<212> TYPE: PRT
<213> ORGANISM: BOVINE

<400> SEQUENCE: 5

Glu Glu Leu Ser Ser Pro Leu Thr Ala His Val Thr Gly Arg Ile Pro
  1               5                  10                  15

Leu Trp Leu Thr Gly Ser Leu Leu Arg Cys Phe Thr Gly Pro Gly Leu
             20                  25                  30

Phe Glu Val Gly Ser Glu Pro Phe Tyr His Leu Phe Asp Gly Gln Ala
         35                  40                  45

Leu Leu His Lys Phe Asp Phe Lys Glu Gly His Val Thr Tyr His Arg
     50                  55                  60

Arg Phe Ile Arg Thr Asp Ala Tyr Val Arg Ala Met Thr Glu Lys Arg
 65                  70                  75                  80

Ile Val Ile Thr Glu Phe Gly Phe Thr Cys Ala Phe Pro Asp Pro
                 85                  90                  95

Cys Lys Asn Ile Phe Ser Arg Phe Phe Ser Tyr Phe Arg Gly Val Glu
                100                 105                 110

Val Thr Asp Asn Ala Leu Val Asn Val Tyr Pro Val Gly Glu Asp Tyr
            115                 120                 125

Tyr Ala Cys Thr Glu Thr Asn Phe Ile Thr Lys Ile Asn Pro Glu Thr
        130                 135                 140

Leu Glu Thr Ile Phe Thr Lys Gln Val Asp Leu Cys Asn Tyr Val Ser
145                 150                 155                 160

Val Asn Gly Ala Thr Ala His Pro His Ile Glu Asn Asp Gly Thr Val
                165                 170                 175

Tyr Asn Ile Gly Asn Cys Phe Gly Lys Asn Phe Ser Ile Ala Tyr Asn
            180                 185                 190

Ile Val Lys Ile Pro Pro Leu Gln Ala Asp Lys Glu Asp Pro Ile Ser
        195                 200                 205

Lys Phe Thr Ser Glu Ile Val Val Gln Phe Pro Cys Ser Asp Arg Phe
210                 215                 220

Lys Pro Ser Tyr Val His Ser Phe Gly Leu Thr Pro Asn Tyr Ile Val
225                 230                 235                 240

Phe Val Glu Thr Pro Val Lys Ile Asn Leu Phe Lys Phe Leu Ser Ser
                245                 250                 255

Trp Ser Leu Trp Gly Ala Asn Tyr Met Asp Cys Phe Glu Ser Phe Thr
            260                 265                 270

Asn Glu Thr Met Gly Val Trp Leu His Ile Ala Asp Lys Lys Arg Lys
        275                 280                 285

Lys Tyr Leu Asn Asn Lys Tyr Arg Thr Ser Pro Phe Asn Leu Phe His
    290                 295                 300

His Ile Asn Thr Tyr Glu Asp Asn Gly Phe Leu Ile Val Asp Leu Cys
305                 310                 315                 320

Cys Trp Lys Gly Phe Glu Phe Val Tyr Asn Tyr Phe Thr Leu Tyr Leu
                325                 330                 335

Ala Asn Leu Arg Glu Asn Trp Glu Glu Val Lys Lys Asn Ala Arg Lys
            340                 345                 350
```

-continued

```
Ala Pro Gln Pro Glu Val Arg Arg Tyr Val Leu Pro Leu Asn Ile Asp
        355                 360                 365

Lys Ala Asp Thr Gly Lys Asn Leu Val Thr Leu Pro Asn Thr Thr Ala
        370                 375                 380

Thr Ala Ile Leu Cys Ser Asp Glu Phe Thr Thr Ile Trp Leu Glu Pro
385                 390                 395                 400

Glu Val Leu Phe Ser Gly Pro Arg Gln Ala Phe Glu Phe Pro Gln Ile
                405                 410                 415

Asn Tyr Gln Lys Tyr Cys Gly Lys Pro Tyr Thr Tyr Ala Tyr Gly Leu
            420                 425                 430

Gly Leu Asn His Phe Val Pro Asp Arg Leu Cys Lys Leu Asn Val Lys
        435                 440                 445

Thr Lys Glu Thr Trp Phe Thr Val Trp Gln Gly Pro Asp Ser Tyr Pro
    450                 455                 460

Ser Glu Pro Ile Phe Val Ser His Pro Asp Ala Leu Glu Glu Asp Asp
465                 470                 475                 480

Gly Val Val Leu Ser Val Val Ser Pro Gly Ala Gly Gln Lys Pro
                485                 490                 495

Ala Tyr Leu Leu Ile Leu Asn Ala Lys Asp Leu Ser Glu Val Ala Arg
        500                 505                 510

Ala Glu Phe Thr Val Glu Ile Asn Ile Pro Val Thr Phe His Gly Leu
        515                 520                 525

Phe
```

<210> SEQ ID NO 6
<211> LENGTH: 18
<212> TYPE: PRT
<213> ORGANISM: CHICKEN

<400> SEQUENCE: 6

```
Asn Lys Glu Glu His Pro Glu Pro Ile Lys Ala Glu Val Gln Gly Gln
  1               5                  10                  15

Leu Pro
```

<210> SEQ ID NO 7
<211> LENGTH: 18
<212> TYPE: PRT
<213> ORGANISM: CHICKEN

<400> SEQUENCE: 7

```
Asn Lys Glu Glu His Pro Glu Pro Ile Lys Ala Glu Val Gln Gly Gln
  1               5                  10                  15

Leu Pro
```

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (18)
<223> OTHER INFORMATION: i

<400> SEQUENCE: 8
aacaargarg ascayccnga                                              20

-continued

```
<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (7)
<223> OTHER INFORMATION: i
<220> FEATURE:
<221> NAME/KEY: modified_base
<222> LOCATION: (13)
<223> OTHER INFORMATION: i

<400> SEQUENCE: 9
sagctgnccc tgnacytcsg c                                           21

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 10
tctgaattcc ggagcccata aaagc                                       25
```

The invention being thus described, it will be obvious that the same may be varied in many ways. Such variations are not to be regarded as a departure from the spirit and scope of the invention and all such modifications are intended to be included within the scope of the following claims.

What is claimed is:

1. An isolated nucleic acid sequence encoding a polypeptide of SEQ ID NO: 1.

2. An isolated nucleic acid sequence according to claim 1 wherein the nucleic acid is a deoxyribonucleic acid.

3. An isolated nucleic acid sequence comprising an antisense ribonucleic acid, which binds to the nucleic acid sequence according to claim 1.

4. A primer for amplifying a gene coding for the polypeptide of SEQ ID NO:1 which primer consists essentially of a fragment of the nucleic acid sequence according to claim 1.

5. A probe for detecting a gene coding for the polypeptide of SEQ ID NO:1 which probe consists essentially of a fragment of the nucleic acid sequence according to claim 1.

6. A test kit for amplifying and/or detecting a gene or a fragment thereof coding for the polypeptide of SEQ ID NO:1 wherein the test kit comprises at least one primer according to claim 4.

7. A test kit for amplifying and/or detecting a gene or a fragment thereof coding for the polypeptide of SEQ ID NO:1 wherein the test kit comprises at least one probe according to claim 5.

8. A method for introducing a cDNA coding for the polypeptide of SEQ ID NO:1 into a host cell comprising introducing a cDNA coding for the polypeptide of SEQ ID NO:1 into a vector suitable for the host cell and introducing the vector into the host cell.

9. A method according to claim 8 wherein the host cell is a plant cell.

10. A method according to claim 8 wherein the host cell is a prokaryotic cell.

11. A method according to claim 8 wherein the host cell is a yeast cell or a fungal cell.

12. A method according to claim 8 wherein the host cell is an alga cell.

13. A method according to claim 8 wherein the host cell is a mammalian cell.

14. A method according to claim 13 wherein the mammalian cell is a human cell.

15. A host cell obtained by the method of claim 8.

16. A host cell according to claim 15 which comprises a heterologous cDNA coding for the polypeptide of SEQ ID NO:1.

17. An isolated polynucleotide which encodes the polypeptide of SEQ ID NO: 1 comprising SEQ ID NO:2.

18. An isolated polynucleotide according to claim 17 which consists essentially of SEQ ID NO: 2.

19. An isolated polynucleotide according to claim 17 which consists of SEQ ID NO: 2.

20. A vector comprising the polynucleotide of SEQ ID NO: 2.

21. A host cell transformed with the vector of claim 20.

22. A primer set for amplifying a polynucleotide encoding the polypeptide of SEQ ID NO:1 comprising SEQ ID NO:8 as a 5' primer and SEQ ID NO: 9 as a 3' primer.

23. A primer set for amplifying a polynucleotide encoding the polypeptide of SEQ ID NO:1 comprising a polyT/Not reverse primer and SEQ ID NO:10 as a forward primer.

24. A kit for amplifying and/or detecting a polypeptide or fragment thereof encoding the polypeptide of SEQ ID NO:1 comprising at least one primer selected from the group consisting of SEQ ID NOs:8,9, and 10.

* * * * *